(12) United States Patent
Habermann et al.

(10) Patent No.: US 8,048,854 B2
(45) Date of Patent: Nov. 1, 2011

(54) AMIDATED INSULIN GLARGINE

(75) Inventors: Paul Habermann, Frankfurt am Main (DE); Frank Zocher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/349,864

(22) Filed: Jan. 7, 2009

(65) Prior Publication Data

US 2009/0176692 A1 Jul. 9, 2009

Related U.S. Application Data

(63) Continuation of application No. PCT/EP2007/005932, filed on Jul. 5, 2007.

(30) Foreign Application Priority Data

Jul. 11, 2006 (DE) .......................... 10 2006 031 962

(51) Int. Cl.
*A61K 38/28* (2006.01)
*C07K 14/62* (2006.01)

(52) U.S. Cl. ............ 514/6.3; 514/6.2; 514/6.5; 514/7.2; 514/11.7; 530/303; 530/308

(58) Field of Classification Search .......................... None
See application file for complete search history.

(56) References Cited

U.S. PATENT DOCUMENTS

| | | | |
|---|---|---|---|
| 5,227,293 A | 7/1993 | Stengelin et al. | |
| 5,656,722 A | 8/1997 | Dorschug et al. | |
| 5,663,291 A | 9/1997 | Obermeier et al. | |
| 6,528,486 B1 * | 3/2003 | Larsen et al. | 514/12 |
| 6,875,589 B1 | 4/2005 | Dorschug et al. | |
| 2006/0120969 A1 * | 6/2006 | Nilsson et al. | 424/46 |

FOREIGN PATENT DOCUMENTS

| | | |
|---|---|---|
| EP | 0132769 | 2/1985 |
| EP | 0214826 | 3/1987 |
| EP | 0254516 | 1/1988 |
| EP | 0294851 | 12/1988 |
| EP | 0140084 | 6/1990 |
| EP | 0229998 | 7/1992 |
| EP | 0376156 | 3/1996 |
| WO | WO 01/04156 | 1/2001 |
| WO | WO 02/066628 | 8/2002 |
| WO | WO 02/068660 | 9/2002 |
| WO | WO 02/070722 | 9/2002 |
| WO | WO 03/044210 | 5/2003 |
| WO | WO 03/105888 | 12/2003 |
| WO | WO 2004/005342 | 1/2004 |
| WO | WO 2006/015879 | 2/2006 |
| WO | WO 2006/058620 | 6/2006 |
| WO | WO 2007/036299 | 4/2007 |

OTHER PUBLICATIONS

Barnett, A., et. al., Insulin Analogues, The Lancet, vol. 349, pp. 47-51, (1997).

Hartmann, H., et. al., Biological Activity of des-B26-1330)-Insulinamide and Related Analogues in Rat Hepatocyte Cultures, Diabetologia, (1989), vol. 32, pp. 416-420.

Leyer et al, The role of the C-terminus of the insulin B-chain in modulating structural and functional properties of the hormone, International Journal of Peptide & Protein Research, vol. 46, No. 5, Nov. 1995, pp. 397-407.

Sanger, F., et. al., The Amide Groups of Insulin, The Biochemical Journal, (1955) vol. 59, No. 3, pp. 509-518.

Schellenberger et al., Attempts for Quanitfying the S' Subsite Specificity of Serine Proteases, Advances in the Biosciences, Peptides and Proteases: Recent Advances; Selected Papers Presented At the 2nd International Meeting on the Molecular and Cellular Regulation of Enzyme Activity, vol. 65, (1987), pp. 159-166.

Schellenberger et al., Protease-Catalyzed Kinetically Controlled Peptide Synthesis, Angewante Chemie, International Ediition, vol. 30, No. 11, 1991, pp. 1437-1449.

The Effect of Intensive Treatment of Diabetes on the Developement and Progression of Long-Term Complications in Insulin-Dependent Diabetes Mellitus, The New England Journal of Medicine vol. 329, No. 14, pp. 977-986 (1993).

* cited by examiner

*Primary Examiner* — David Romeo
(74) *Attorney, Agent, or Firm* — Scully, Scott, Murphy & Presser, P.C.

(57) ABSTRACT

The invention relates to insulin glargine which is modified by amidation, especially Gly(A21), Arg(B31), Arg amide (B32) human insulin (insulin glargine amide).

8 Claims, 1 Drawing Sheet

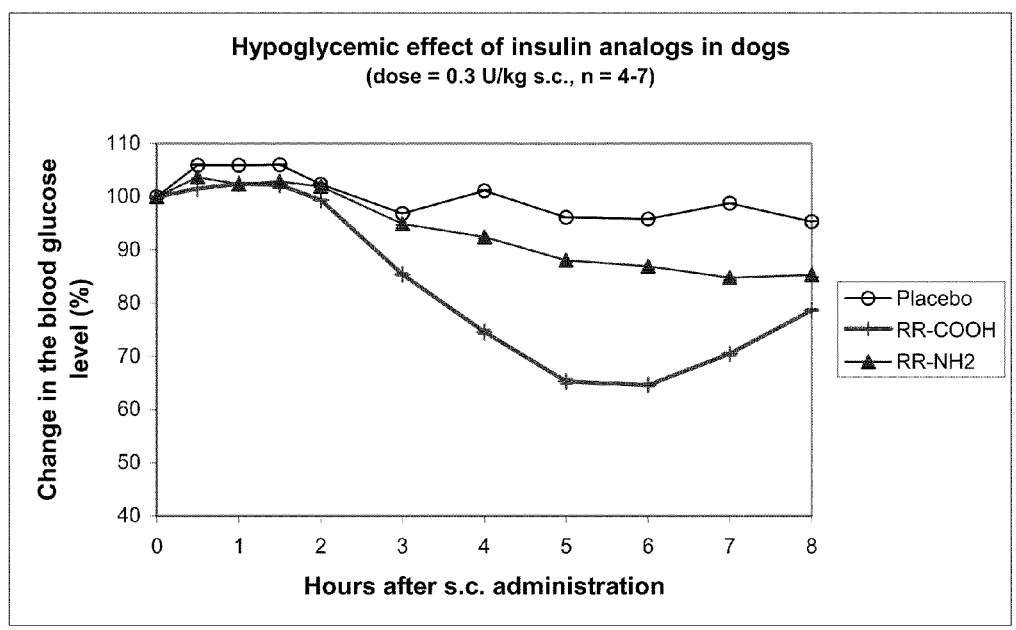

SEQUENCE LISTING

<160> NUMBER OF SEQ ID NOS: 9

<210> SEQ ID NO 1
<211> LENGTH: 45
<212> TYPE: DNA
<213> ORGANISM: Artificial
<220> FEATURE:
<223> OTHER INFORMATION: Primer ins_gly_a21_rev

<400> SEQUENCE: 1 tttttccat gggtcgacta tcagccacag tagttttcca gctgg            45

<210> SEQ ID NO 2
<211> LENGTH: 48
<212> TYPE: DNA
<213> ORGANISM: Artificial
<220> FEATURE:
<223> OTHER INFORMATION: Primer alpha_insf1

<400> SEQUENCE: 2 tttttggat cctttggaat aaaagatttg ttaaccaaca cttgtgtg           48

<210> SEQ ID NO 3
<211> LENGTH: 44
<212> TYPE: DNA
<213> ORGANISM: Artificial
<220> FEATURE:
<223> OTHER INFORMATION: Primer ins_gly_rev2

<400> SEQUENCE: 3 tttttccat gggtcgctat cagccacagt agttttccag ctgg              44

<210> SEQ ID NO 4
<211> LENGTH: 49
<212> TYPE: DNA
<213> ORGANISM: Artificial
<220> FEATURE:

<223> OTHER INFORMATION: Primer ins_gly_rev2

<400> SEQUENCE: 4
tttttggcgc cgaattcact actattagcc acagtagttt tccagctgg        49

<210> SEQ ID NO 5
<211> LENGTH: 40
<212> TYPE: DNA
<213> ORGANISM: Artificial
<220> FEATURE:
<223> OTHER INFORMATION: Primer pich_insgly_dirf

<400> SEQUENCE: 5 tttttttctcg agaaaagatt tgttaaccaa cacttgtgtg                  40

<210> SEQ ID NO 6
<211> LENGTH: 33
<212> TYPE: DNA
<213> ORGANISM: Artificial
<220> FEATURE:
<223> OTHER INFORMATION: Primer pich_insgly_dirrev

<400> SEQUENCE: 6 tttttttggcg ccgaattcac tactattagc cac                        33

<210> SEQ ID NO 7
<211> LENGTH: 49
<212> TYPE: DNA
<213> ORGANISM: Artificial
<220> FEATURE:
<223> OTHER INFORMATION: Primer a29_a30_k31f

<400> SEQUENCE: 7
gtttcttcta cactccaaag gcggctaaag gtatcgttga acaatgttg         49

<210> SEQ ID NO 8
<211> LENGTH: 49
<212> TYPE: DNA
<213> ORGANISM: Artificial
<220> FEATURE:
<223> OTHER INFORMATION: Primer a29_a30_k31rev

<400> SEQUENCE: 8
caacattgtt caacgatacc tttagccgcc tttggagtgt agaagaaac         49

<210> SEQ ID NO 9
<211> LENGTH: 48
<212> TYPE: DNA
<213> ORGANISM: Artificial
<220> FEATURE:
<223> OTHER INFORMATION: Primer alpha_insf1

<400> SEQUENCE: 9 tttttttggat cctttggaat aaaagatttg ttaaccaaca cttgtgtg        48

AMIDATED INSULIN GLARGINE

This application is a continuation of International application No. PCT/EP2007/005932, filed Jul. 5, 2007, which is incorporated herein by reference in its entirety; which claims the benefit of priority of German Patent Application No. 10 2006 031 962.1, filed Jul. 11, 2006.

DESCRIPTION

The invention relates to an insulin glargine which has been modified by amidation, in particular Gly(A21), Arg(B31), Arg-amide (B32) human insulin (insulin glargine amide).

About 177 million people around the world suffer from Diabetes mellitus. These include about 17 million type I diabetics for whom replacement of the lacking endocrine insulin secretion is the only possible therapy at present. Those affected are dependent on insulin injections, usually several times a day, throughout life. Type II diabetes contrasts with type I diabetes in that there is not always a deficiency of insulin, but in a large number of cases, especially in the advanced stage, treatment with insulin, where appropriate combined with an oral antidiabetic, is regarded as the most favorable type of therapy.

In healthy people, insulin release by beta cells in the pancreas is strictly coupled to the blood glucose concentration. Elevated blood glucose levels like those occurring after meals are rapidly compensated by a corresponding rise in insulin secretion. In the fasting state, the plasma insulin level falls to a baseline value which suffices to ensure a continuous supply of glucose to insulin-sensitive organs and tissues and to keep hepatic glucose production low during the night. Replacement of the endogenous insulin secretion by exogenous, usually subcutaneous administration of insulin usually does not come close to the quality of the physiological regulation of blood glucose described above. Upward or downward derangements of the blood glucose level are frequent since diabetics incorrectly judge the respective situation. However, in addition, elevated blood glucose levels lasting for years represent, even without initial symptoms, a considerable health risk. The large-scale DCCT study in the USA (The Diabetes Control and Complications Trial Research Group (1993) N. Engl. J. Med. 329, 977-986) unambiguously proved that chronically elevated blood glucose levels are substantially responsible for the development of late diabetic complications. Late diabetic complications are micro- and macrovascular damage which in some circumstances becomes manifest as retinopathy, nephropathy or neuropathy and leads to blindness, renal failure and loss of extremities and, in addition, is associated with an increased risk of cardiovascular disorders. It is to be inferred therefrom that an improved therapy of diabetes must primarily aim at keeping blood glucose as closely as possible within the physiological range. The intensive insulin therapy policy intends to achieve this by injections several times a day of fast- and slow-acting insulin preparations. Fast-acting formulations are given at meal times in order to compensate the postprandial rise in blood glucose. Slow-acting basal insulins are intended to ensure the basic supply of insulin especially during the night without leading to hypoglycemia.

Insulin is a polypeptide composed of 51 amino acids divided into 2 amino acid chains: the A chain with 21 amino acid and the B chain with 30 amino acids. The chains are linked together by 2 disulfide bridges. Insulin preparations have been employed for many years for the therapy of diabetes. Moreover, not only are naturally occurring insulins used, but more recently also insulin derivatives and analogs.

Insulin analogs are analogs of naturally occurring insulins, namely human insulin or animal insulins, which differ by replacement of at least one naturally occurring amino acid residue by other amino acid residues and/or addition/deletion of at least one amino acid residue from the corresponding, otherwise identical naturally occurring insulin. U.S. Pat. No. 5,656,722 for example describes for example insulin glargine (Arg(B31), Arg(B32), Gly(A21) human insulin). The added and/or replaced amino acid residues may also be those which do not occur naturally.

Insulin derivatives are derivatives of naturally occurring insulins or insulin analogs in which one or more amino acid residues and/or the N or C termini of the A and/or B chain are replaced by functional groups. The functional groups are selected from a group comprising amide residues, amine residues, carboxyl residues, alkyl residues, alcohol residues and alkoxy residues.

An efficient insulin therapy makes use of so-called basal insulins. By these are meant formulations which make slow, continuous release of exogenously administered insulin possible. In this way, a baseline insulin concentration in the body which has advantageous effects on the physiological condition of the person suffering from diabetes is achieved over a lengthy period. Ideally, the onset of the effect of insulin is delayed and has a time/effect profile which is as flat as possible, so that the risk of short-term hypoglycemia is distinctly minimized and administration can take place without previous intake of foodstuffs.

The recombinant insulin analog Arg(B31), Arg(B32), Gly (A21) human insulin (insulin glargine; U.S. Pat. No. 5,656, 722) is in this connection notable in many patients for needing to be supplied to the body only every 24 hours—i.e. only once a day, in order to achieve a basal effect. Control of blood glucose is improved, leading for example to a reduction in the Hba1c level.

It has now surprisingly been found that insulin glargine amide which results from amidation of arginine in position B32 of insulin glargine shows a time/effect profile which is distinctly more flat and thus more advantageous than insulin glargine itself. At the onset of action, the blood glucose level falls without a marked lowest point (nadir). This means that insulin glargine amide has a surprisingly advantageous quality in the pharmacological sense. The risk of hypoglycemia on administration is thus minimized. Administration of insulin glargine amide sets up a normally fasting blood glucose level of 70-110 mg/dl glucose. In addition, insulin glargine amide surprisingly shows a prolonged effect compared with insulin glargine. The invention thus relates to insulin glargine amide.

The skilled worker is clear in this connection that the insulin glargine amide relates to a pharmaceutical formulation. By this is meant a pharmaceutical mixture which advantageously displays in the best manner the effect of insulin glargine amide after administration. Aqueous solutions are regarded as basis in this connection. Further components must be appropriately miscible. It is advantageous that the preparation was not intended to comprise any components derived from animal sources. The risk of viral contamination is thus minimized. It is further advantageous to prevent microbial contamination by adding preservatives. It is possible by adding isotonic agents to compensate a possible adverse effect of the formulation on the physiology of the tissue cells at the administration site. Addition of protamine may have stabilizing effects, so that substantially salt-free insulin preparation can be obtained via addition of protamine to the formulation. Addition of a phenolic component may lead to stabilization of the hexamer structure of the insulin analog and thus favors the delaying effect on the onset of action. Glargine amide can be given in parallel to fast-acting insulins such as APIDRA® (insulin glulisine), NOVORAPID® (insulin aspart), HUMALOG® (insulin lispro) or insulin derivatives undergoing development or formulations with a corresponding time/action profile. It is clear to the skilled worker in this connection that appropriately formulated mixtures of the respective insulin components can also be used for this purpose. The amide can moreover preferably be taken by individuals who use inhalable insulin such as EXUBERA®. Glargine amide can further be used in pharmaceutical preparations which comprise peptides described by an activity comparable to that of GLP-1 (glucagon like peptide-1). Such peptides are exemplified by GLP-1 (7-37), Exenatide (BYETTA®) or peptides whose preparation described in the patent applications WO 2006/058620, WO 2001/04156 and WO 2004/005342.

WO 2008/006497A1 patent application entitled "Method for producing insulin analogs with dibasic B chain terminus" which was filed on the same date as this patent application describes inter alia a method for preparing insulin glargine amide. This entails addition of argininamide by a trypsin-catalyzed ligation onto Gly(A21), Arg(B31) human insulin with high yield. It is possible in this case to control the reaction so that the preferred product is the insulin analog of the form Gly(A21), Arg(B31), Arg(B32)-amide. There are descriptions in the literature of the possibilities that, in particular, protected arginine derivatives are unstable in various solvents. For this reason, new protective groups which bring about an improved stability are continually being developed in peptide chemistry. A positive influence on the yield is possible by varying the reaction conditions according to the protective groups or amide group. This is familiar to the skilled worker and the invention also relates thereto. U.S. Pat. No. 5,656,722 describes the plasmids pB40 and pINT91d which allow the expression of miniproinsulin as part of a fusion protein. Replacement of asparagine in position 21 of the insulin A chain by glycine allows Arg(B31), Gly(A21) miniproinsulin to be prepared directly from these fusion proteins, and it can be converted directly after tryptic digestion into the precursor for preparing insulin glargine amide. Corresponding fusion proteins need not necessarily be prepared intracellularly. It is clear to the skilled worker that this proinsulin analog can also be prepared by bacterial expression with subsequent secretion into the periplasma and/or into the culture supernatant. European patent application EP-A 1 364 029 describes this by way of example. The invention also relates to the use of Arg(B31), Gly(A21) human insulin precursors which result directly after expression from such bacterial methods.

Amidation of insulin analogs can generally take place at various points. Insulin glargine in which the C-terminal carboxyl group is amidated is referred to as insulin glargine amide.

It is further familiar to the skilled worker that the expression systems described by way of example represent only a small segment of the host/vector system developed for the recombinant preparation of proteins. Host/vector systems permitting the preparation of target peptides thus also form part of the invention.

The present invention thus relates to amidated insulin glargine, in particular amidated insulin glargine of the form Gly(A21), Arg(B31), Arg(B32)-$NH_2$ human insulin (insulin glargine amide).

The invention further relates to a method for preparing an amidated insulin glargine amide, in particular insulin glargine amide, where a precursor of insulin glargine amide in the form Gly(A21), Arg(B31) human insulin is prepared recombinantly, a coupling is carried out with argininamide in the presence of an enzyme having trypsin activity, and the insulin glargine amide is isolated.

The invention further relates to the use of insulin glargine amide in a method for manufacturing a medicament for the treatment of diabetes, especially diabetes of type I or type II diabetes.

The invention further relates to a pharmaceutical comprising insulin glargine amide which represents in particular an aqueous formulation or a powder.

The pharmaceutical is a pharmaceutical preparation which is preferably a solution or suspension for injection purposes; it is characterized by a content of at least one amidated insulin glargine, in particular insulin glargine amide, and/or at least one of the physiologically tolerated salts thereof in dissolved, amorphous and/or crystalline—preferably in dissolved—form.

The preparation preferably has a pH of between about 2.5 and 8.5, in particular between about 4.0 and 8.5,
comprises a suitable tonicity agent,
a suitable preservative
and where appropriate a suitable buffer,
and preferably also a particular zinc ion concentration,
the whole naturally in sterile aqueous solution. The preparation carrier forms a totality of the ingredient of the preparation apart from the active ingredient.

Suitable tonicity agents are for example glycerol, glucose, mannitol, NaCl, calcium or magnesium compounds such as $CaCl_2$ etc.

The solubility of the amidated insulin glargine or of its physiologically tolerated salt is influenced by the choice of the tonicity agent and/or preservative at the weakly acidic pH values.

Suitable preservatives are for example phenol, m-cresol, benzyl alcohol and/or p-hydroxybenzoic esters.

Buffer substances which can be used, in particular to setup a pH of between about 4.0 and 8.5, are for example sodium acetate, sodium citrate, sodium phosphate etc. Otherwise, physiologically acceptable dilute acids (typically HCl) or alkalis (typically NaOH) are also suitable for setting up the pH.

If the preparation has a zinc content, one of from 1 µg/ml to 2 mg/ml, in particular from 5 µg to 200 µg of zinc/ml, is preferred.

For the purpose of varying the active ingredient profile of the preparation of the invention, it is also possible to admix unmodified insulin, preferably bovine, porcine or human insulin, in particular human insulin, or insulin analogs and derivatives thereof. It is likewise possible to admix one or more exendin-4 derivatives or peptides which are characterized by an activity comparable to that of GLP-1 (glucagon like peptide-1). The invention likewise relates to such pharmaceuticals (preparations).

Preferred active ingredient concentrations are those corresponding to about 1-1500, further preferably about 5-1000 and especially about 40-400 international units/ml.

BRIEF DESCRIPTION OF THE DRAWINGS

FIG. 1 shows hypoglycemic effect of various insulin analogs in dogs. Wherein RR—COOH=insulin glargine and RR—NH$_2$=insulin glargine amide.

The invention is described in more detail below by the examples without being restricted thereto.

EXAMPLE 1

Gene Sequence for Secretion of a Hirudin Arg(B31), Gly(A21) Insulin Fusion Protein by Baker's Yeast The patent application EP-A 1 364 032 proposes the use of hirudin as fusion partner for the expression and secretion of pharmaceutically interesting proteins of value in yeasts.

Example 1 of the patent application EP-A 1 364 032 describes a host-vector system for preparing a fusion protein consisting of a hirudin derivative and miniproinsulin. This system can be used to prepare miniproinsulins which lead as precursor to the claimed insulin glargine amide.

The expression vector is constructed in analogy to the example of the patent application EP-A 1 364 032 by replacing the primer insnco1rev and thus altering the codon in position A21.

The following primer is synthesized to prepare the sequence coding for a fusion protein comprising miniproinsulin (with Gly(A21), Arg(B31) human insulin being produced later from the miniproinsulin):

```
ins_gly_a21_rev
                                       (SEQ ID NO.: 1)
    TTTTTTCCATGGGTCGACTATCAGCCACAGTAGTTTTCCAGCTGG
```

The primer in this case completely covers the gene segment coding for amino acids A15-A21 of the insulin analog. Combining this primer with the primer SEQ ID NO: 4 from example 1 of the patent application EP-A 1 364 032 and using the plasmid pADH2Hir_ins as template allows generation by PCR of a DNA fragment that, after digestion with the restriction enzymes KpnI and NcoI, is inserted into the correspondingly opened expression vector and comprises the desired fusion protein.

The vector is designated pADH2Hir_ins_glyA21. The fusion protein is expressed in accordance with example 3 of the patent application EP-A 1 364 032 and processed to Gly(A21)-miniproinsulin in accordance with example 6, and purified by cation exchange chromatography. The material of the fraction which contains miniproinsulin is used to prepare Gly(A21), Arg(B31), Arg(B32)-NH$_2$ human insulin as in example 5 of the present application.

EXAMPLE 2

Gene Sequence for Direct Secretion of the Gly(A21), Arg(B31), Human Insulin Precursor by Baker's Yeast DNA of the plasmid pADH2Hir_ins_glyA21 described in example 7 of the patent application EP-A 1 364 032 is used to prepare a vector construct for direct secretion of Gly(A21), Arg(B31) human insulin.

The following primers are synthesized.

```
alpha_insf1
5'-TTTTTTGGATCCTTTGGAATAAAAGATTTGTTAACCAACACTTGTGTG-3'  (SEQ ID NO.: 2)
```

It covers the sequence encoding the C terminus of the alpha-factor, codons for Lys-Arg and of the N-terminus of the miniproinsulin sequence.

```
ins_gly_rev2
5'-TTTTTTCCAT GGGTCGCTAT CAGCCACAGT AGTTTTCCAG CTGG -3'  (SEQ ID NO.: 3)
```

The primer hybridizes with the 3' end of the insulin analog sequence cloned into the plasmid pADH2Hir_ins_glyA21. A PCR (standard conditions) generates a DNA fragment which, after digestion with the restriction enzymes KpnI and NcoI, is inserted into the correspondingly opened expression vector and comprises the desired fusion protein. The in competent cells of the yeast strain Y79 transforms. Transformants are subsequently expressed as described in example 7 of the aforementioned patent application.

Gly(A21), Arg(B31)-miniproinsulin is concentrated in accordance with EP-A 0 347 781, example 9, and, after trypsin cleavage, purified by cation exchange chromatography. Material of the fraction which contains miniproinsulin is used to prepare Gly(A21), Arg(B31), Arg(B32) human insulin as in example 5 of the present application.

EXAMPLE 3

Gene Sequence for Secretion of a Hirudin-Gly(A21), Arg(B31) Human Insulin Fusion Protein by *Pichia pastoris*

Cloning of the expression vector takes place in analogy to example 4 of the patent application EP-A 1 364 032. Instead of the sequence primer *pichia*_H_Irev2, in this case the primer ins_gly_rev2 is employed and later enables the possibility of expression of Gly(A21) human insulin with the PCR product:

5'-TTTTTGGCGCCGAATTCACTACTATTAGCCACAGTAGTTTTCCAGCTGG-3' (SEQ ID NO.:4)

The resulting plasmid is designated pPich_Hir_ins-GlyA21. Purification of Gly(A21), Arg(B31)-miniproinsulin as starting material is carried out as described.

EXAMPLE 4
Gene Sequence for Direct Secretion of the Gly(A21), Arg(B31) Precursor by *Pichia pastoris*

The appropriate expression vector is constructed in analogy to example 7 of the patent application EP-A 1 364 032. The DNA of the plasmid pPich_Hir_ins-GlyA21 and two primers pich_insgly_dirf and pich_insgly_dirrev are required.

pich_insgly_dirf
(SEQ ID NO.: 5)
5'-TTTTTTCTCGAGAAAAGATTTGTTAACCAACACTTGTGTG-3' pich_insgly_dirrev
(SEQ ID NO.: 6)
5'-TTTTTT GGCGCCGAATTCACTACTATTAGCCAC-3'

Purification of Gly(A21), Arg(B31)-miniproinsulin as starting material is carried out as described.

EXAMPLE 5

Preparation of Gly(A21), Arg(B31), Arg(B32)-NH$_2$-Human Insulin from a Gly(A21), Arg(B31) Human Insulin Precursor by Coupling with Argininamide 100 mg of Gly(A21), Arg(B31) human insulin which has been prepared as in examples 1-4 are dissolved in 0.95 ml of argininamide solution (446 g/L), and 0.13 mL of M Na acetate buffer (pH 5.8) and 2 ml of DMF are added. The reaction mixture is cooled to 12° C. and started by adding 0.094 ml of trypsin (0.075 mg, Roche Diagnostics).

After 8 h, the reaction is stopped by adding TFA to a pH 2.5 and analyzed by HPLC. >60% Gly(A21), Arg(B31), Arg (B32) human insulin is formed. The amidated analog (insulin glargine amide) is purified after addition of trypsin inhibitor solution in analogy to U.S. Pat. No. 5,656,722.

EXAMPLE 6

Gene Sequence for Direct Secretion of a Lys(B31) Precursor by Baker's Yeast

Two primers are synthesized and serve to introduce the sequence Ala(B30), Ala(C1), Lys(C2):

a29_a30_k31f
5'-GTTTCTTCTACACTCCAAAGGCGGCTAAAGGTATCGTTGAACAATGTTG-3' (SEQ ID NO.: 7)
and a29_a30_k31rev
5'-CAACATTGTT CAACGATACC TTTAGCCGCC TTTGGAGTGT AGAAGAAAC-3' (SEQ ID NO.: 8)

The primer alpha_insf1
5'-TTTTTTGGATCCTTTGGAATAAAAGATTTGTTAACCAACACTTGTGTG-3' (SEQ ID NO.: 9)

covers the sequence of the C terminus of the alpha-factor, codons for Lys-Arg and of the N terminus of the miniproinsulin sequence. DNA of the plasmid pADH2Hir_ins from example 1 of the application WO 02/070722A1 serves as template for two polymerase chain reactions. In reaction 1, the primers a29_a30_k31f and insncolrev (SEQ ID NO.: 6 from WO 02/070722A1) are used, and in reaction 2 the primers a29_a30_k31 re and alpha_insf1 are used. The standard reactions are carried out and the resulting PCR fragments are isolated. Aliquots of the two yields are combined and serve as template for a third reaction with the primers insncolrev and SEQ ID NO.: 6 from WO 02/070722A1. The resulting PCR fragment is cloned and expressed as described in example 8. The result is Ala(B31), Ala(C1), Lys(C1)-miniproinsulin, which is converted with lysyl endopeptidase in B(1-29)-A(1-21) split insulin and serves as intermediate for preparing the target protein.

EXAMPLE 7

Reaction with Lysyl Endopeptidase and Thr-Arg(Boc)-Arg(Boc)-NH2

The insulin precursor is reacted as described in DE3844211 with lysyl endopeptidase (LEP) and trypsin, and purified (example 1). For this purpose, 10 mg of insulin precursor are dissolved in Tris buffer (pH 8.0), and LEP from Lysobacter enzymogenes is added (0.01 ml of a 1 mg/ml conc. solution in water, Merckbiosciences). Incubation is carried out at room temperature for 2 h, and purification is by RP-HPLC (Nucleosil 120-5 column). The Gly(A21) B(1-29)-A(1-20) split insulin precursor is reacted with Thr-Arg(Boc)-Arg(Boc)-NH2 following DE3844211. For this purpose, 10 mg of the desthr-insulin precursor are dissolved in 0.25 ml of 10 M acetic acid, and 0.7 ml of 1.5 M Thr-Arg(Boc)-Arg(Boc)-NH2 dissolved in DMSO/1,3-butanediol (1:1) is added. Then 0.15 ml of LEP (15 mg/ml, dissolved in water) is added. The mixture is incubated at room temperature for 2 h. The protein is then precipitated by adding 5 ml of methanol/methyl tert-butyl ether (v/v=1:4) and dried. The protective group is eliminated by adding 1 M HCl/acetic acid and incubating at 0° C.

EXAMPLE 8

Hypoglycemic Effect of Insulin Glargine Amide

The hypoglycemic effect is investigated on healthy male dogs of the Beagle breed. A dose of 0.3 IU/kg of body weight is administered subcutaneously. In a controlled group, dogs are treated with the same dose of insulin glargine, and a further group receives a placebo injection without added insulin. Blood is taken from the animals for blood glucose determination every half hour for the first 2 hours after injection, and then each hour up to the eighth hour. It emerges that insulin glargine amide as well as insulin glargine exhibit a delayed time/effect profile, but the profile of the amide is distinctly advantageous because, on onset of the reaction, the blood glucose level falls without a clear low point (nadir). The result is depicted in FIG. 1.

What is claimed is:

1. Amidated insulin glargine, which is in the form of Gly (A21), Arg(B31), Arg(B32)-$NH_2$ human insulin.

2. A method for the treatment of diabetes in a patient comprising administering to said patient a therapeutically effective amount of amidated insulin glargine as claimed in claim 1.

3. The method as claimed in claim 2, wherein the diabetes is of type I or type II.

4. A pharmaceutical composition comprising the amidated insulin glargine of claim 1, in combination with one or more pharmaceutically acceptable excipients.

5. The pharmaceutical composition as claimed in claim 4, which is an aqueous formulation.

6. The pharmaceutical composition as claimed in claim 4, which is a powder.

7. The pharmaceutical composition as claimed in claim 5, in which the insulin glargine amide is present in dissolved, crystalline and/or amorphous form.

8. The pharmaceutical composition as claimed in claim 4, which additionally comprises one or more exendin-4 derivatives or peptides which are characterized by an activity comparable to that of glucagon like peptide-1 (GLP-1).

* * * * *